US011139070B2

(12) United States Patent
Taniguchi et al.

(10) Patent No.: US 11,139,070 B2
(45) Date of Patent: Oct. 5, 2021

(54) MEDICAL INFORMATION VIRTUAL REALITY SERVER SYSTEM, MEDICAL INFORMATION VIRTUAL REALITY PROGRAM, MEDICAL INFORMATION VIRTUAL REALITY SYSTEM, METHOD OF CREATING MEDICAL INFORMATION VIRTUAL REALITY DATA, AND MEDICAL INFORMATION VIRTUAL REALITY DATA

(71) Applicant: Holoeyes, Inc., Tokyo (JP)

(72) Inventors: Naoji Taniguchi, Tokyo (JP); Maki Sugimoto, Tokyo (JP)

(73) Assignee: Holoeyes, Inc., Tokyo (JP)

( * ) Notice: Subject to any disclaimer, the term of this patent is extended or adjusted under 35 U.S.C. 154(b) by 33 days.

(21) Appl. No.: 16/480,087

(22) PCT Filed: Jan. 23, 2018

(86) PCT No.: PCT/JP2018/002035
§ 371 (c)(1),
(2) Date: Jul. 23, 2019

(87) PCT Pub. No.: WO2018/139468
PCT Pub. Date: Aug. 2, 2018

(65) Prior Publication Data
US 2020/0176104 A1   Jun. 4, 2020

(30) Foreign Application Priority Data
Jan. 25, 2017   (JP) .............................. JP2017-011619

(51) Int. Cl.
*G16H 30/00*   (2018.01)
*G16H 30/40*   (2018.01)
(Continued)

(52) U.S. Cl.
CPC ........... *G16H 30/40* (2018.01); *G06T 7/0014* (2013.01); *G06T 7/11* (2017.01); *G06T 2207/10081* (2013.01); *G06T 2207/10088* (2013.01)

(58) Field of Classification Search
CPC ......... G16H 30/40; G06T 7/11; G06T 7/0014; G06T 2207/10081; G06T 2207/10088
See application file for complete search history.

(56) References Cited

U.S. PATENT DOCUMENTS 6,346,940 B1 * 2/2002 Fukunaga ............... G06T 15/20
345/420
2006/0067573 A1 * 3/2006 Parr ......................... G06K 9/00
382/154
(Continued)

FOREIGN PATENT DOCUMENTS

JP        10234662 A     9/1998
JP     2006527619 A    12/2006
(Continued)

*Primary Examiner* — Khai M Nguyen
(74) *Attorney, Agent, or Firm* — Ogilvie Law Firm

(57) ABSTRACT

A server system facilitates communication between users using three-dimensional data in a virtual reality space, facilitates communication relating to data between joint owners thereof, facilitates protection of privacy and handling of data relating to persons whose data has been acquired, and improves the usability of the data. This server system includes: a means for inputting medical image data; a means for dividing the medical image data into segments for each characteristic part, including living body parts, implants, medical devices, index markers and wearable objects; a means for converting the medical image data into three-dimensional polygon data having segments; a means for tagging the three-dimensional polygon data or the segments; a means for associating the three-dimensional polygon data with an arbitrarily defined world coordinate posi-
(Continued)

tion; and a means for storing the three-dimensional polygon data in a database and outputting the three-dimensional polygon data on the basis of the tags.

16 Claims, 15 Drawing Sheets

(51) Int. Cl.
*G06T 7/11* (2017.01)
*G06T 7/00* (2017.01)

(56) References Cited

U.S. PATENT DOCUMENTS

| | | | | |
|---|---|---|---|---|
| 2010/0322474 | A1* | 12/2010 | Cheriyadat | G06T 7/246 382/103 |
| 2014/0181754 | A1* | 6/2014 | Mori | G06F 19/00 715/847 |
| 2019/0026956 | A1* | 1/2019 | Gausebeck | H04N 13/10 |

FOREIGN PATENT DOCUMENTS

| | | | |
|---|---|---|---|
| JP | 2013521039 | A | 6/2013 |
| JP | 2014050487 | A | 3/2014 |
| JP | 2016508049 | A | 3/2016 |
| JP | 2016112419 | A | 6/2016 |

\* cited by examiner (1)

(2)

MEDICAL INFORMATION VIRTUAL REALITY SERVER SYSTEM, MEDICAL INFORMATION VIRTUAL REALITY PROGRAM, MEDICAL INFORMATION VIRTUAL REALITY SYSTEM, METHOD OF CREATING MEDICAL INFORMATION VIRTUAL REALITY DATA, AND MEDICAL INFORMATION VIRTUAL REALITY DATA

TECHNICAL FIELD

This invention relates to a virtual reality server and virtual reality system for medical application.

BACKGROUND ART

Conventionally, CT (Computed Tomography) and MRI (Magnetic Resonance Imaging) inspections have been largely performed for the diagnosis of diseases. Since there is much medically useful information in the images obtained by CT and MRI inspections, sharing such information among many medical institutions and medical providers is highly useful for medical research and education.

However, CT images and MRI images are managed according to a standard called DICOM (Digital Imaging and Communication in Medicine), and there is a problem that data cannot be easily shared from the viewpoint of privacy protection because personal information of the patient is recorded there. Moreover, in the case of sharing data in general, tagging is performed in order to improve the usability but tagging the information recording the personal information needs to be performed more carefully from the viewpoint of privacy protection because tagging makes access to data easier. Therefore, until now, sharing information of patient's CT images and MRI images has not been conducted across hospital boundaries.

On the other hand, in recent years, advances in technologies related to VR (Virtual Reality) and the like have been remarkable, and in addition to VR, there are concepts such as AR (Augmented Reality) and MR (Mixed Reality).

In that trend, a virtual image restoration system for a Buddha image is known, which is capable of restoring a wooden art object such as a Buddha image using virtual reality. (refer to Patent Literature 1) In this method, a tomographic image is acquired and corrected using a CT scanner, and a plurality of 2-dimensional tomographic images is stacked to construct a 3-dimensional stereoscopic image. Then, the amount of data is reduced by smoothing or a similar technology and converted into a virtual reality image.

However, the virtual image restoration system of Buddha image disclosed in the above-mentioned Patent Document 1 constructs a 3-dimensional image by laminating 2-dimensional tomographic images and performs smoothing etc., but it does not employ an innovation, for example, to perform sorting for easy tagging, which is a problem in terms of the availability and convenience of the data.

In addition, a system that visually supports surgery by synthetically displaying an image of a portion that is intrinsically invisible by using a 3-dimensional digital magnifying glass at the time of surgery is known. (refer to Patent Literature 2)

This is for producing a surface polygon model based on 2-dimensional medical image data. However, the 3-dimensional digital magnifying glass system disclosed in Patent Document 2 has no problem as long as the obtained 3-dimensional data is used for the patient, but in order to share data with a large number of users, an innovation to improve the usability of the 3D image is necessary but this kind of innovation has not been seen, which is a problem.

Under the present circumstances, when 2-dimensional medical image data is used as a 3-dimensional image data and a virtual reality space is created, there is no innovation to obtain segmented data in order to enhance the usability of the data.

PRIOR ART

Patent Literature

[Patent Literature 1] JP2002-216102A
[Patent Literature 2] WO2009/116663

OUTLINE OF THE INVENTION

Problems to be Solved by the Invention

In view of such a situation, it is an object of the present invention to provide a medical information virtual reality server system which facilitates communication between users using three-dimensional data employed in a virtual reality space, facilitates communication relating to data between joint owners thereof, is also suitable for facilitating protection of privacy and handling of data relating to persons whose data has been acquired, and also improves the usability of the data.

Means to Solve the Objects

Thus, a medical information virtual reality server system of the present invention comprises the following means in a virtual reality system.
1) Data input means for inputting medical image data,
2) Segmentation means for segmenting medical image data into segments for each characteristic site including a living body site, an implant, a medical device, an index marker or amounting object,
3) 3-dimensional data conversion means for converting medical image data into 3-dimensional polygon data having segments,
4) Tagging means for tagging 3-dimensional polygon data or segments,
5) Coordinate relating means for relating 3D polygon data to an arbitrary world coordinate position,
6) Data output means for storing 3D polygon data in a database and outputting based on the attached tag.

In the medical information virtual reality server system of the present invention, the medical image data is preferably at least either one of 2-dimensional medical image data including CT image data, MRI image data or ultrasound image data, and 3-dimensional position measurement data of a characteristic site. Here, 2-dimensional medical image data includes simple X-ray image data and the like, and 3-dimensional position measurement data includes, for example, data acquired by an infrared scanner.

In the medical information virtual reality server system of the present invention, a biological part to be divided into segments is intended to include not only a part of the human body but also a part of an animal, which is at least one of the following: organs, blood vessels, lesions, nerves, membranes, or liquid including blood.

Moreover, a medical device broadly includes a medical instrument and a medical apparatus that could be imaged along with a living body, with examples of a medical instrument being a scalpel, forceps and such, and examples of medical apparatus being an artificial respirator and such.

An example of an index marker is an article or the like provided to indicate an incision in surgery, and an example of a wearing article is a garment worn by a subject.

In the medical information virtual reality server system of the present invention, as a means for classifying into segments, a means for segmenting medical image data into segments is provided. Conventionally, in medical images, judgments as to what is cancer and what is blood vessel have been made only manually. However, for example, segmentation can be performed more efficiently by automatically segmenting 2-dimensional medical image data. Therefore, the means for dividing into segments here includes both automatic means and manual means.

Also, by providing means for associating 3-dimensional polygon data with any world coordinate position, 3-dimensional polygon data is associated with world coordinate position at any position, and multiple users share the same space at the same time, making it possible to experience the virtual reality space.

The medical information virtual reality server system of the present invention preferably further comprises a personal information deletion means for deleting personal information linked to medical image data.

For example, a CT image is usually tagged with personal information such as the name of a subject. Therefore, sharing CT images as they are across the boundaries of a medical institution poses a problem in terms of protection of the privacy of individuals. Therefore, means are provided for deleting personal information tagged to 2-dimensional medical image data, which allows data to be shared among many medical institutions.

As to the segmentation means in the medical information virtual reality server system of this invention, when the medical image data is 2-dimensional medical image data, it is preferable to section into segments based on differences in image density or 3-dimensional position coordinate information. By sectioning into segments based on the differences in image density or 3-dimensional position coordinate information, segmentation with high accuracy becomes possible.

In the medical information virtual reality server system of the present invention, the segmentation means preferably further comprises a means for correcting segments of 3-dimensional polygon data and sectioning into corrected segments. By providing a means for correcting the segments of the 3-dimensional polygon data and dividing them into corrected segments, more accurate classification becomes possible. Means for dividing into segments includes either an automatic means or a manual means.

In the medical information virtual reality server system according to the present invention, the segmentation means preferably further comprises a means for correcting the segment based on the medical image data divided into segments and dividing the segments into corrected segments. The segmentation here includes not only automatic segmentation by image processing of a computer, but also manual segmentation performed by a healthcare provider, which enables highly accurate segmentation.

In this way, not only a means for dividing 2-dimensional medical image data and 3-dimensional polygon data into segments is provided, but also a means for evaluating and correcting the divided segments is provided, so that the results obtained by an operator's segmentation are learned, making it possible to improve the accuracy of automatic classification.

The 3-dimensional polygon data is composed of 3-dimensional coordinates, so each coordinate can be tagged, and it is also possible to tag divided segments. Furthermore, it is also possible to tag a plurality of coordinates or segments together.

As described above, because the data can be managed by segmentation after patterning with tagging, search becomes easier and convenience for the user is improved and it also makes it easy to distribute and accumulate the data in the community of the sharer.

The medical information virtual reality server system according to the present invention preferably stores the 3-dimensional polygon data and a change on a time series between 3-dimensional polygon data obtained by transforming medical image data in the past regarding the same subject as the 3-dimensional data and as a set of time series data, in the data base.

By using a virtual reality system, it becomes possible to manage the elapsed time by digitization. That is, even if it is 3-dimensional polygon data of a specific subject, for example, the pathological condition may change depending on the passage of time, like perioperative one year before, or one year after the operation. By storing such data in a database, it becomes possible to compare disease states.

The medical information virtual reality server system of the present invention preferably stores shape changes associated with time changes of 3-dimensional polygon data as a set of time series data in a database. Unlike the time-series change of 3-dimensional polygon data, for example, by storing the shape change associated with a short time change such as a heartbeat as a set of time series data, it becomes possible to create a more accurate and realistic virtual reality space.

The medical information virtual reality server system according to the present invention can store the visual field and action of the user in the virtual reality space using 3D polygon data as a set of time series data in association with time series data of 3D polygon data in a database. In the virtual reality system, since it is possible to intuitively convey the user's vision and actions to other users, the non-verbal know-how of the expert which has been difficult to explain in words up to now can be taught just by letting other users experience the system.

The medical information virtual reality server system according to the present invention can also store the change of the 3-dimensional shape of a feature part accompanying a user's flexural deformation in a virtual reality space using a 3-dimensional polygon data as a set of time series data in a database by relating to the time series data of the 3-dimensional polygon data.

For example, in the case of organs and bones, the hardness, elasticity, etc. differ depending on the living body part, so the 3-dimensional shape of the living body part changes in various ways according to the deformation operation such as the separation operation or the connection operation of the user. Moreover, for training or simulation, for example, processing such as distorting or cutting only a segment corresponding to a certain organ may be required. The utility of the data can be further enhanced by storing such changes in shape as a set of time series data in association with the time series data of 3-dimensional polygon data and storing them in a database.

In a 3-dimensional data conversion means of the medical information virtual reality server system according to the present invention, it is preferable to have a polygon data addition means for adding or superimposing 3-dimensional polygon data generated from data other than the medical image data to be an origin of the converged 3-dimensional polygon data. For example, by adding or superimposing medical equipment that did not exist at the time of filming medical images, simulation and such supposing an actual operation becomes easier, which improves the user's convenience.

Moreover, the 3-dimensional data conversion means is preferably provided with a means for deleting a part or all of the converted 3-dimensional polygon data.

The medical information virtual reality program according to the present invention causes a computer to function as a data input means, a segment classification means, a 3-dimensional data conversion means, a tagging means, and a data output means in the above-mentioned medical information virtual reality server system.

The medical information virtual reality system of the present invention comprises a client terminal for displaying a virtual reality space interactively to a user and a medical information virtual reality server system connected via a network to transmit and receive data. The client terminal transmits the tag information input by a user to the medical information virtual reality server system. The medical information virtual reality server system extracts 3-dimensional polygon data based on the received tag information and transmits them to the client terminal. The client terminal configures and displays a virtual reality space based on the received 3-dimensional polygon data, and records and transmits the user's motion in the virtual reality space and change of the virtual reality space based on the motion to the medical information virtual reality server system.

Here, the motion of the user includes not only the movement of the hand but also the movement of the viewpoint. Therefore, not only can the virtual reality space be displayed on the client terminal, but also the user's actions and the like in the virtual reality space are recorded and stored in the server, and for example, it becomes easy for young practitioners to learn the viewpoints and movements of a veteran operator based on the recorded data.

Also, in the medical information virtual reality system of the present invention, at least one mobile terminal is connected via a wire or wirelessly to the client terminal, and transmits data constituting the virtual reality space created in the client terminal to the mobile terminal. On the mobile terminal, the virtual reality space based on the received data is displayed so that the virtual reality space displayed on the mobile terminal and the virtual reality space displayed on the client terminal share the same virtual reality space.

The PC, the head mounted display, the controller, etc. used for the virtual reality system are very expensive, so it has been difficult for many people to use these devices simultaneously in real time, but by installing the application on a smartphone and the like, a lot of people can share among themselves the sense obtained by the virtual reality space inexpensively and easily. Here, the mobile terminal refers to a smartphone, a tablet terminal, a mobile phone, a mobile PC, and the like. The client terminal is not limited to devices such as a desktop PC, for example, and a mobile terminal such as a tablet terminal can be used as a client terminal.

In a specific method, the application is installed on the client terminal and the mobile terminal, respectively, and connected through the network. Here, as a network, a wireless communication technology such as Bluetooth (registered trademark) is preferably used, but other methods may be used.

The position information of a head mounted display and a controller connected to the client terminal via a wire or wirelessly is transmitted from the client terminal to the mobile terminal, and the same virtual reality space as the virtual reality space on the client terminal viewed by a user can be viewed on a mobile terminal. By synchronizing the position information of the controller, not only the field of view but also the movement of the user's hand using the controller can be viewed in real time on the mobile terminal. Namely, the user using the client terminal and the user using the mobile terminal can recognize the virtual reality space matching the respective position information while sharing the same virtual reality space.

Although in some cases, as a virtual reality space displayed on the client terminal or the mobile terminal, a virtual reality space matching each position information is displayed, in a case wherein the position of the mobile terminal cannot be acquired, for example, the configuration may be such that a virtual reality space similar to the virtual reality space matching to the position information of the client terminal at the mobile terminal may be displayed.

A method of creating medical information virtual reality data of the present invention comprises the following steps.
1) a segment sectioning step for sectioning into a segment for each feature part by using at least either one of medical image data such as a 2-dimensional medical image data of CT image data, MRI image data or ultrasonic image data and 3-dimensional position measurement data such as a biological part, an implant, a medical device, an index marker or a 3-dimensional position measurement data of a feature part of the furnished object;
2) a 3-dimensional data conversion step for converting medical image data into 3-dimensional polygon data having segments;
3) a tagging step for tagging 3D polygon data or segments;
4) a coordinate associating step for associating 3-dimensional polygon data with an arbitrary world coordinate position.

Furthermore, it is preferable that a method of creating medical information virtual reality data of the present invention further comprises a personal information deletion step of deleting personal information linked to medical image data.

Moreover, a method of creating medical information virtual reality data of the present invention is preferably further furnished with a step for correlating the user's behavior in the virtual reality space configured based on the 3-dimensional polygon data and the time series data recording the change of the virtual reality space based on the behavior to the time series data of the 3-dimensional polygon data.

Here, the change of the virtual reality space based on the user's action is, for example, the movement of a virtual scalpel manipulated by the user in the virtual reality space or the shape change of the organ cut by the virtual scalpel, and is intended to widely include the change in the virtual reality space other than the user's operation.

In addition, a step for storing the change in time series between the data produced by the method described above and the 3-dimensional polygon data obtained by converting the past medical image data regarding the same subject as a set of time series data in a data base may be provided.

The medical information virtual reality data of the present invention is produced by any of the above methods of creating medical information virtual reality data.

Effects of the Invention

According to the medical information virtual reality server system of the present invention, non-verbal knowledge possessed by a skilled healthcare provider can be easily transmitted to other healthcare providers or subjects, etc. during learning, training or simulation, with an effect of facilitating communication. Further, since the amount of the 3-dimensional polygon data is light, the calculation processing cost can be suppressed, and the service can be provided at a lower cost. Moreover, since the subject's personal information is not stored in the database, privacy can also be protected.

BEST MODE FOR CARRYING OUT THE INVENTION

Embodiments of the present invention will be described in detail below with reference to the drawings. The present invention is not limited to the following embodiments and examples shown in the figures, and the present invention can be various changed in design.

Embodiment 1

Figure 1:
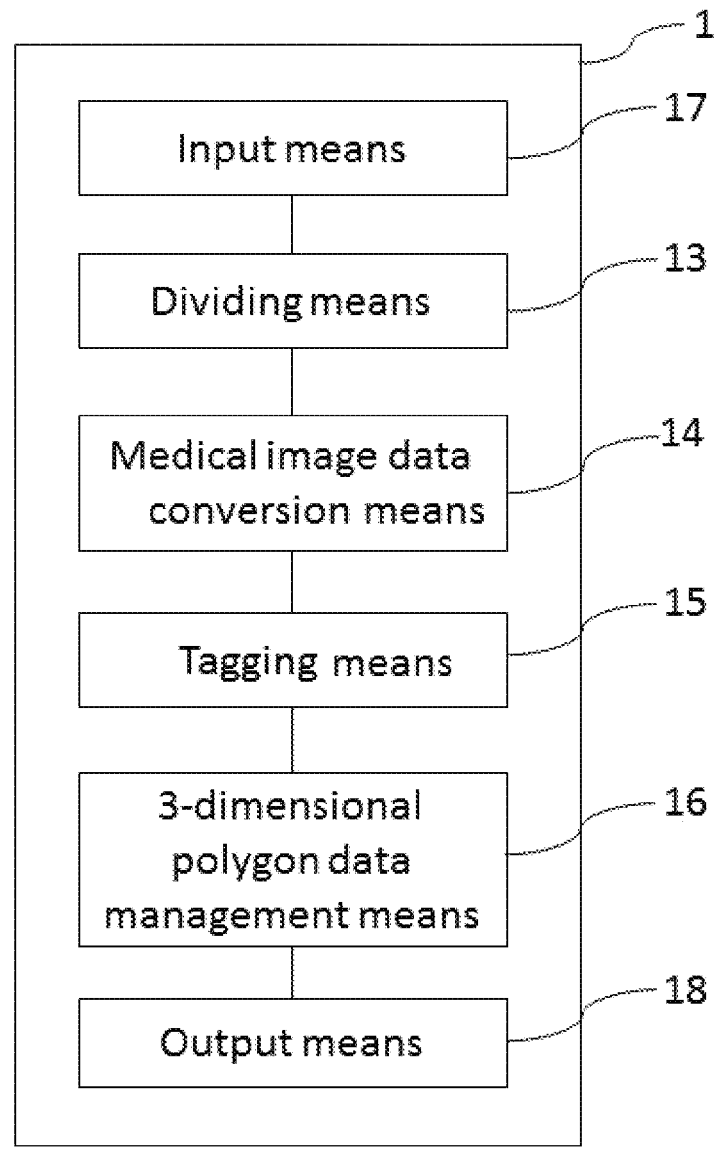
FIG. 1 shows functional block diagram 1 of the medical information virtual reality server system of Embodiment 1.
Figure 2:
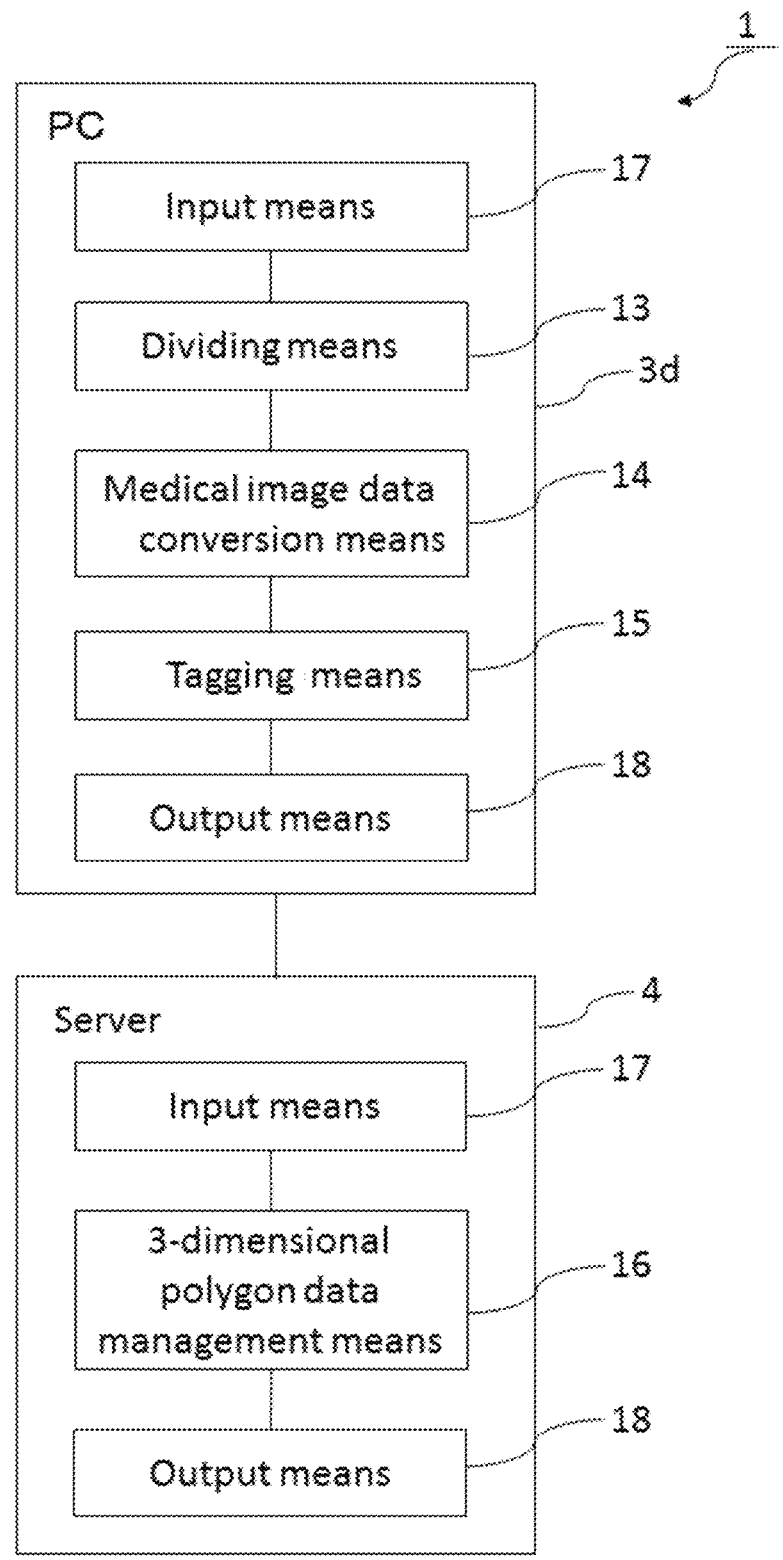
FIG. 2 shows functional block diagram 2 of the medical information virtual reality server system of Embodiment 1.

FIGS. 1 and 2 show functional block diagrams of the medical information virtual reality server system of Embodiment 1.

As shown in FIG. 1, the medical information virtual reality server system 1 of the present embodiment is provided with an input means 17, a dividing means 13, a medical image data conversion means 14, a tagging means 15, a 3-dimensional polygon data management means 16 and an output means 18.

The medical information virtual reality server system 1 does not have to be configured with only one computer, and may be configured with PCs and servers connected via a wire or wirelessly. For example, as shown in FIG. 2, the system may be configured with the PC 3d and the server 4. Here, the PC 3d and the server 4 are provided with an input means 17 and an output means 18, respectively, and are configured to be communicable with other devices. In addition, a plurality of PCs and servers may be provided.

Further, although not shown here, the medical information virtual reality server system 1 is provided with a coordinate associating means, and the user can correlate the 3-dimensional polygon data with an arbitrary coordinate position on occasion to experience the virtual reality space using the 3-dimensional polygon data.

Note that the input means and the output means in the PC and the server are the same as in the following embodiments, and the description thereof is omitted in the second and the subsequent embodiments.

Figure 3:
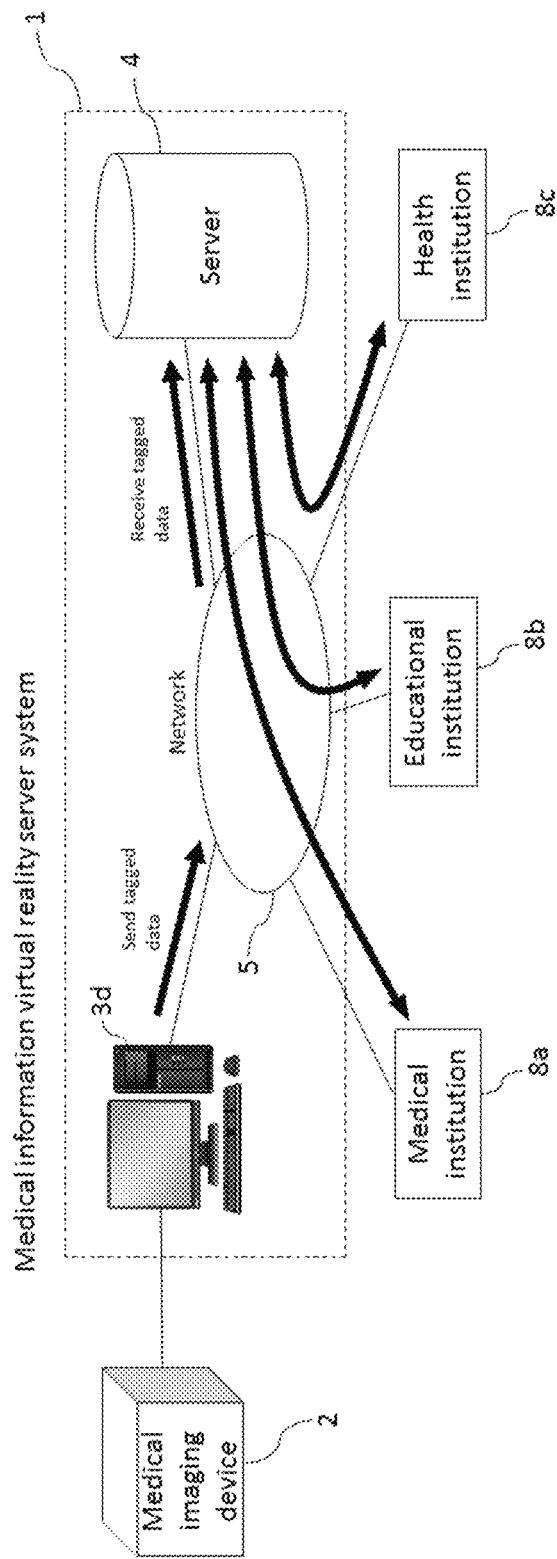
FIG. 3 shows a system configuration diagram of the medical information virtual reality server system of Embodiment 1.

FIG. 3 shows a system configuration diagram of the medical information virtual reality server system of Embodiment 1. As shown in FIG. 3, the medical information virtual reality server system 1 includes a PC 3d and a server 4, and the PC 3d and the server 4 are connected to the network 5. Medical image data is input from the medical imaging apparatus 2 to the PC 3d, and as shown in FIG. 2, the 3-dimensional polygon data is divided by the dividing means 13 into segments for each living body region, medical instrument or medical device. Medical image data is converted into 3-dimensional polygon data by the medical image data conversion means 14 provided in the PC 3d. The tagging means 15 tags 3-dimensional polygon data or segments. The tagged 3-dimensional polygon data is sent to the server 4 via the network 5 as shown in FIG. 3. In the server 4, the 3-dimensional polygon data management means 16 shown in FIG. 2 stores the 3-dimensional polygon data in the database and outputs the data based on the tag.

As shown in FIG. 3, the 3-dimensional polygon data is output according to the user's request. Here, a medical institution 8a, an educational institution 8b, and a health institution 8c are illustrated as users.

Note that, a medical institution, an educational institution, or a health institution is shown as an example here, but the user to be shared is not limited to this, and other users such as for-profit companies and individuals are also targeted. Further, since the network 5 shares the system, a plurality of medical institutions, research and educational institutions, etc. can be added.

Embodiment 2

Figure 4:
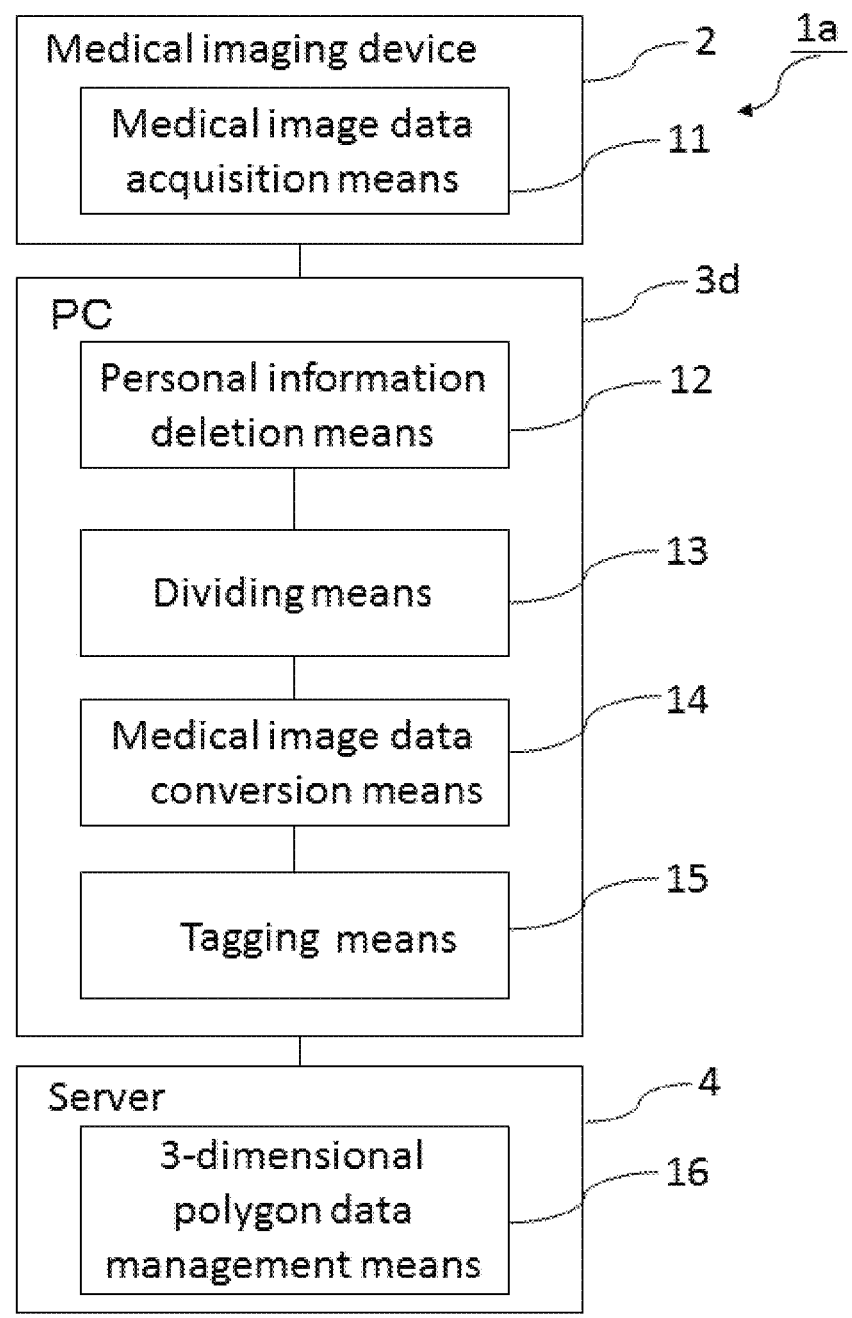
FIG. 4 shows a functional block diagram of the medical information virtual reality system of Embodiment 2.

FIG. 4 shows a functional block diagram of the medical information virtual reality system of Embodiment 2.

As shown in FIG. 4, the medical information virtual reality system 1a according to this embodiment includes a medical imaging apparatus 2, a PC 3d and a server 4.

The medical image capturing apparatus 2 is furnished with a medical image data acquisition means 11. The PC 3d is furnished with a personal information deletion means 12, a dividing means 13, a medical image data conversion means 14 and a tagging means 15. Further, the server 4 is furnished with a 3-dimensional polygon data management means 16.

Figure 5:
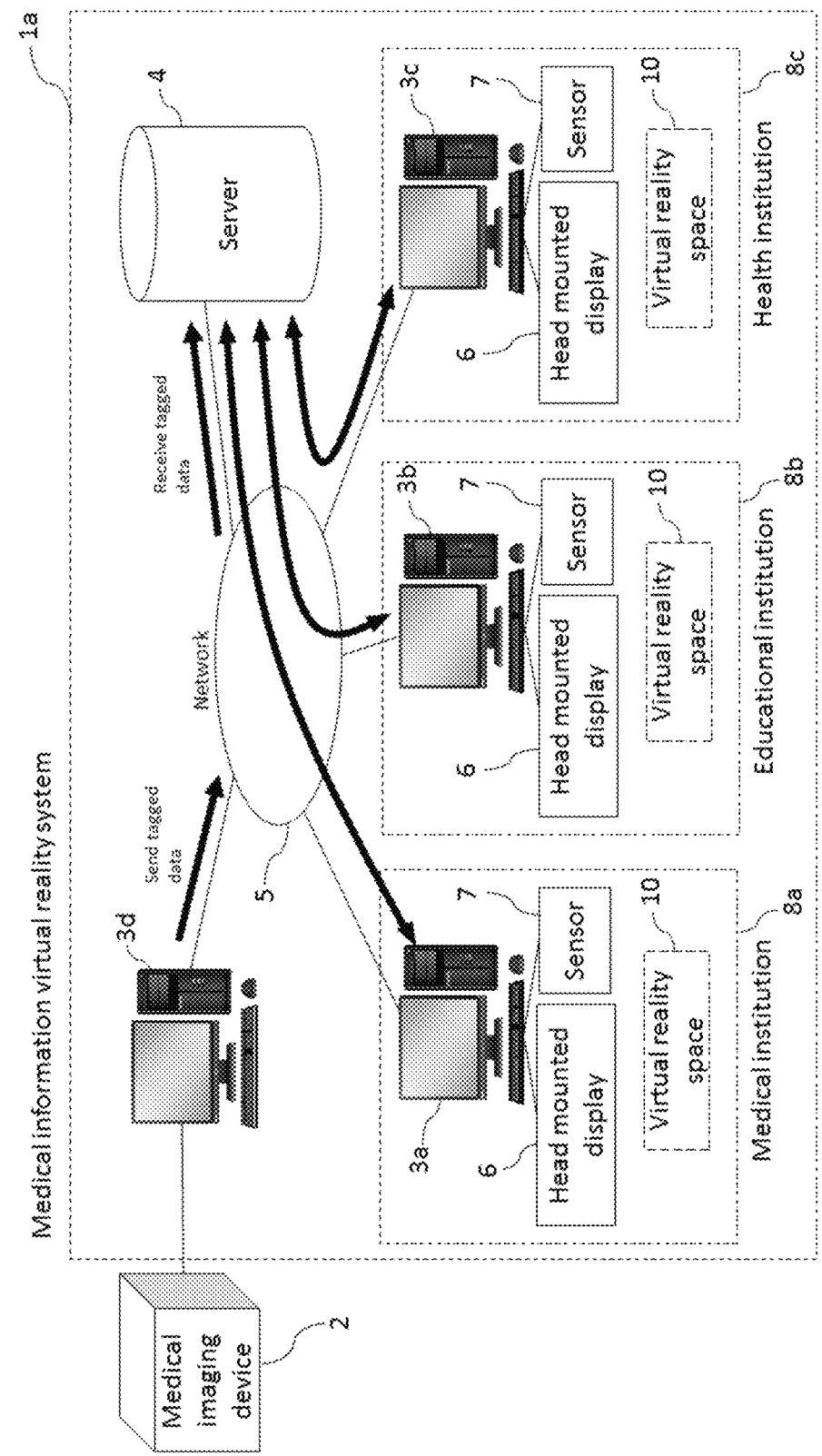
FIG. 5 shows a system configuration diagram of a medical information virtual reality system of Embodiment 2.

FIG. 5 shows a system configuration diagram of a medical information virtual reality system of Embodiment 2.

As shown in FIG. 5, the medical information virtual reality system 1a comprises a PC (3a to 3d), a server 4, a network 5, a head mounted display 6, and a sensor 7.

In the medical image capturing apparatus 2, as shown in FIG. 4, medical image data of a subject to be a target of medical image acquisition is acquired using the medical image data acquisition means 11. Personal information is deleted from the acquired medical image data by a personal information deleting means 12 furnished in the PC 3d. Further, the dividing means 13 divides the 3-dimensional polygon data into segments for each living body part, a medical device or a medical apparatus. Medical image data is converted into 3-dimensional polygon data by the medical image data conversion means 14 furnished in the PC 3d. The tagging means tags 3-dimensional polygon data or 3-dimensional polygon segments. The tagged 3-dimensional polygon data is sent to the server 4 via the network 5 as shown in FIG. 5. In the server 4, the 3-dimensional polygon data management means 16 shown in FIG. 4 stores the 3-dimensional polygon data in the database and the data is output based on the tag.

The medical institution 8a is furnished with a PC 3a, the educational institution 8b is furnished with a PC 3b, and the health institution 8c is furnished with a PC 3c. Although the subject did not receive imaging of the medical image at the medical institution 8a, the educational institution 8b or the health institution 8c, the data is stored in the server 4 in a state where the subject's personal information is deleted, making it possible to search and use said data by the tag in any one of the medical institution 8a, the educational institution 8b, and the health institution 8c. Furthermore, an embodiment may be configured in such a way wherein medical image data, for example, may be acquired by a medical imaging apparatus furnished in a medical institution 8a and personal information may be deleted using a personal information deletion means provided in advance inside of the PC 3a.

When the data stored in the server 4 is output by the tag in the medical institution 8a, the user can experience the virtual reality space 10 by using the head mounted display 6 and the sensor 7 connected with PC 3a via a wire or wirelessly. The data experiencing the virtual reality space 10 is tagged automatically by PC 3a or manually by PC3a or by an attached controller (not shown) connected with PC3a via a wire or wirelessly, and is sent to the server 4 and stored via a network 5. By a repetition of the system usage in such a way, the data utilization by users is accumulated and accordingly a database with higher usability can be constructed.

Embodiment 3

Figure 6:
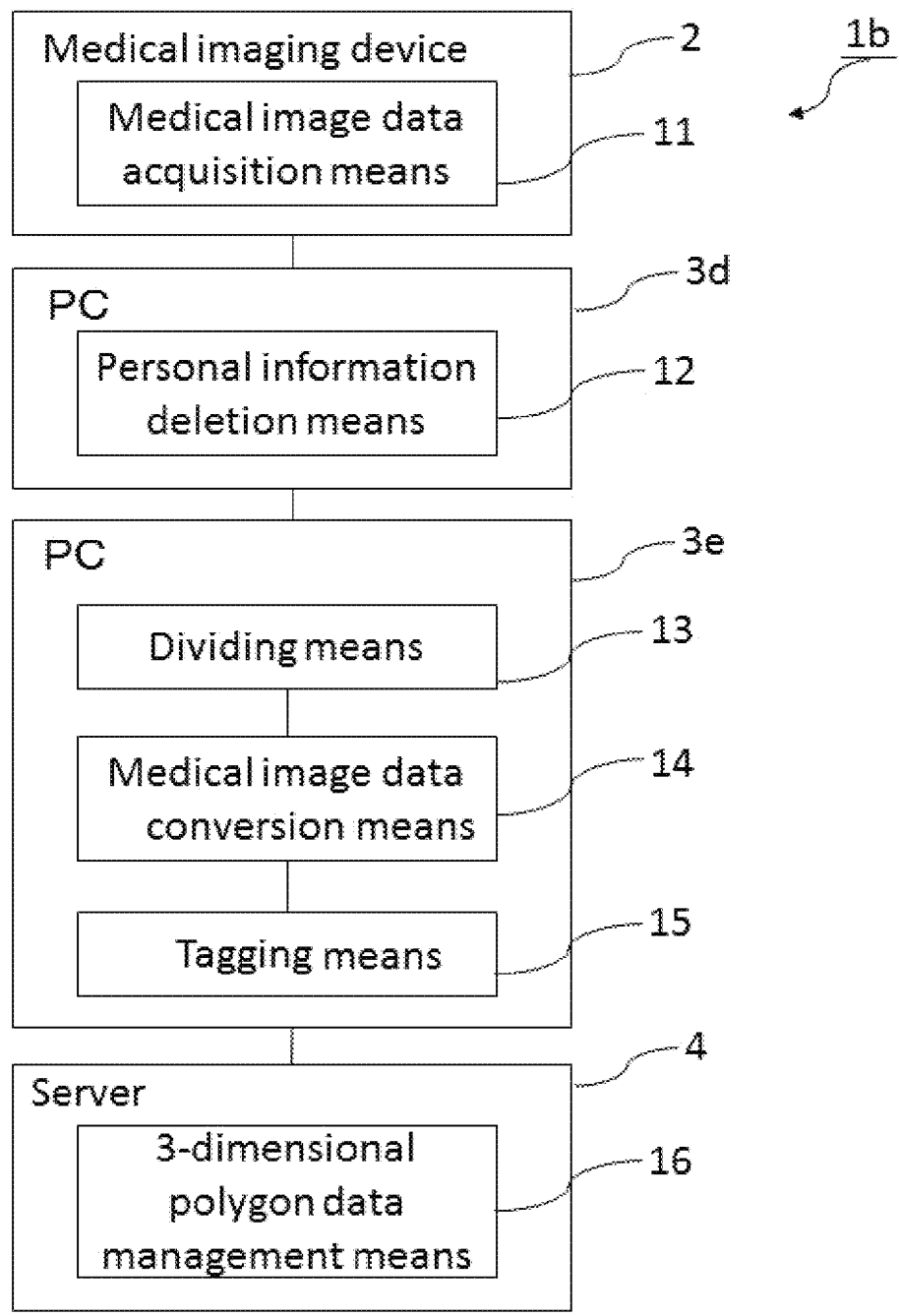
FIG. 6 shows the functional block diagram of the medical information virtual reality system of Embodiment 3.

FIG. 6 shows the functional block diagram of the medical information virtual reality system of Embodiment 3. As shown in FIG. 6, the medical information virtual reality system 1b of the present embodiment is composed of a PC (3d, 3e) and a server 4.

The medical image pickup device 2 is furnished with a medical image data acquisition means 11. The personal information deletion means 12 is provided in the PC 3d. Further, the PC 3e is furnished with a dividing means 13, a medical image data conversion means 14, and a tagging means 15. The server 4 is furnished with a 3-dimensional polygon data management means 16.

Figure 7:
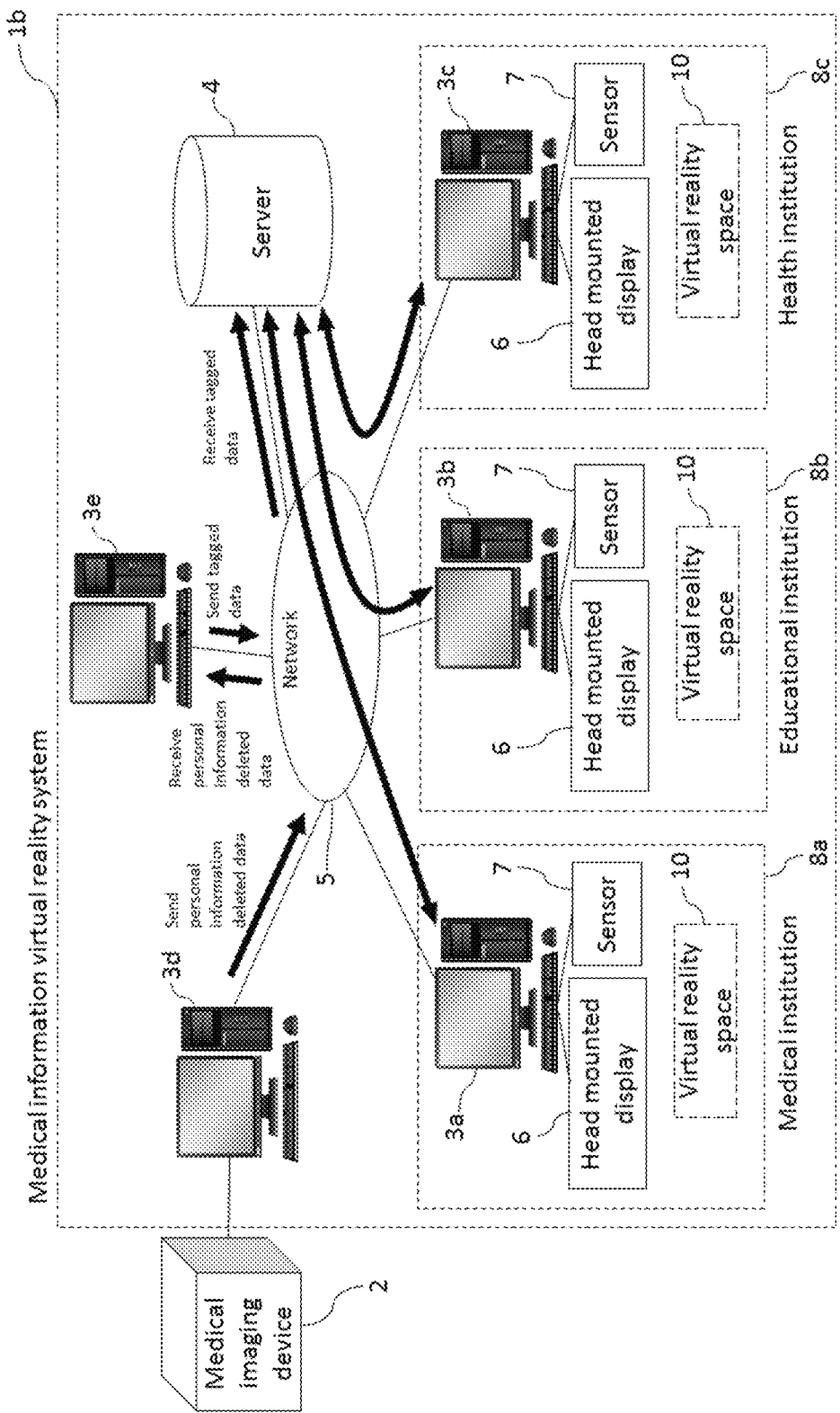
FIG. 7 shows a system configuration diagram of the medical information virtual reality system of Embodiment 3.

FIG. 7 shows a system configuration diagram of the medical information virtual reality system of Embodiment 3. As shown in FIG. 7, the medical information virtual reality system 1b is comprised of a medical imaging device 2, PCs (3a to 3e), a server 4, a network 5, a head mounted display 6 and a sensor 7.

In the medical imaging apparatus 2, as shown in FIG. 6, the medical image data of a subject to be a target of the medical image acquisition is acquired using the medical image data acquisition means 11. The acquired medical image data has its personal information deleted by the personal information deleting means 12 provided in the PC 3d, and is sent to the PC 3e via the network 5 as shown in FIG. 7. In the PC 3e, the 3-dimensional polygon data is divided into segments for each living body region by a dividing means 13 shown in FIG. 6. A medical image data conversion means 14 converts medical image data into 3-dimensional polygon data. The tagging means 15 tags the 3-dimensional polygon data or segments. The 3-dimensional polygon data is stored in a database provided in the server 4 by the 3-dimensional polygon data managing means 16 and is made able to be output by a tag.

A means for deleting personal information from medical image data is provided in PC 3d connected to the medical image pickup apparatus 2 via a wire or wirelessly, and personal information is cut off in the PC 3d. In this state, it is connected to the Internet 5, and privacy protection is achieved. The means for converting medical image data into 3-dimensional polygon data is not necessarily provided in the PC 3d connected to the medical image pickup device 2 via a wire or wirelessly, but unlike this, it may be provided in the PC 3e or the server 4 via the Internet 5.

The medical institutions 8a, the educational institutions 8b, and the health institutions 8c are each provided with a PC (3a to 3c), and can experience the virtual reality space as in Embodiment 2.

Figure 8:
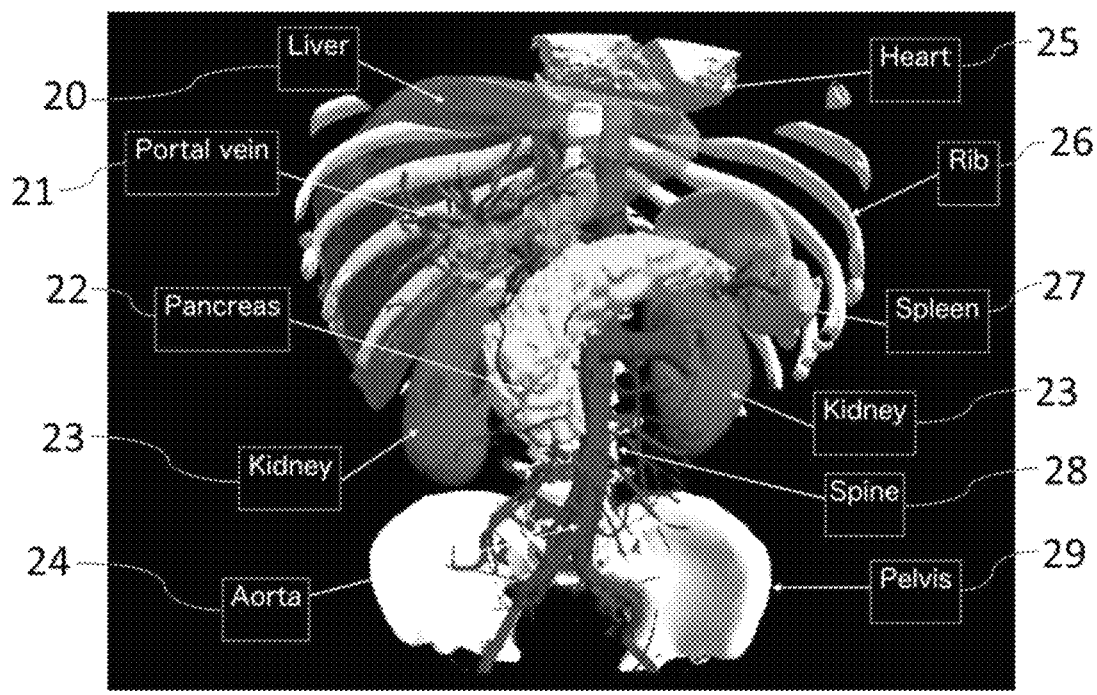
FIG. 8 is an image view of the 3-dimensional polygon data divided into segments for the upper limbs of a human body, (1) showing a front view, and (2) showing a perspective enlarged view.
Figure 8:

FIG. 8 is an image view of the 3-dimensional polygon data divided into segments for the upper limbs of a human body, (1) showing a front view, and (2) showing a perspective enlarged view. As shown in FIG. 8 (1), in the image, the liver 20, portal vein 21, pancreas 22, kidney 23, aorta 24, heart 25, ribs 26, spleen 27, spine 28 and pelvis 29 are segmented and displayed. Also, each part is divided into segments, and the names of the parts are tagged. Therefore, as shown in FIG. 8 (1), the name of each part is displayed by a text, and it is displayed by the arrow so that it can be clearly recognized which segment is which part. As described above, the biological part is color-coded and displayed, and the name of each site is displayed as text, thereby improving the visibility and the usability of data.

FIG. 8 (2) shows a state in which the image shown in FIG. 8 (1) is enlarged and viewed from slightly below. As shown in FIG. 8 (2), the pancreas 22, the kidney 23, the spleen 27 and the gallbladder 30 are segmented and displayed. Since the segment of each part is stored and managed as 3-dimensional polygon data, the name of each part is displayed to indicate the respective part even if the viewing angle is changed, as shown in FIG. 8 (2). Further, in FIG. 8 (2), the gallbladder 30 which is not displayed in FIG. 8 (1) is displayed. In this way, depending on the display angle or the like, it is possible to display an image that is easy for the user to view and understand, such as displaying only the name of the part that is considered to be necessary, or displaying all of them.

Figure 11:
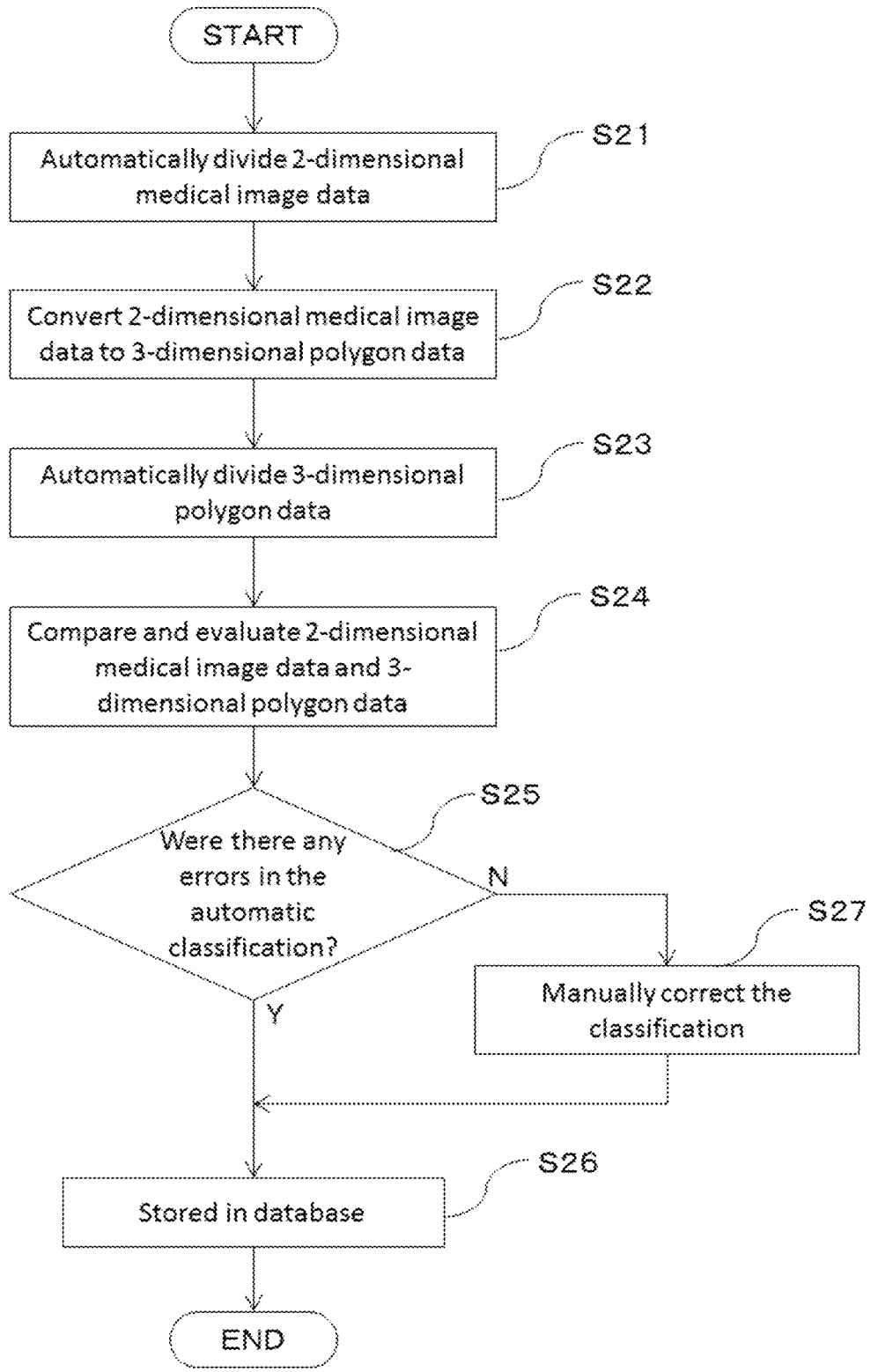
FIG. 11 shows a flow diagram of medical image data segmentation.

A method of such segmentation is described by referring to FIG. 11. FIG. 11 shows a flow diagram of medical image data segmentation.

As shown in FIG. 11, firstly, the 2-dimensional medical image data is automatically divided (S21). The 2-dimensional medical image data is converted to 3-dimensional polygon data (S22). The 3-dimensional polygon data is automatically divided (S23). Both the automatic segmentation based on the 2-dimensional medical image data and the automatic segmentation based on the 3-dimensional polygon data may be performed as shown in this embodiment, or only one of them may be performed.

The 2-dimensional medical image data and the 3-dimensional polygon data are compared and evaluated (S24). If there is no error in the automatic classification (S25), the classification result is stored in the database (S26). If there is an error in the automatic classification, the classification is manually corrected (S27). For example, in a case where a specific organ or blood vessel is the problem based on the information of the medical provider under the circumstance that 3-dimensional polygon data is produced, the applicable portion in the 3-dimensional polygon data is marked. If it is not clear which organ, or tumor, etc. is the problem, from the knowledge of the medical provider, the relevant part in the 3-dimensional polygon data is marked by comparing with the 2-dimensional medical image data of the part corresponding to the relevant part.

As a specific decision factor of the classification, the gradation difference of the image or the 3-dimensional position coordinate information becomes an important decision factor.

In addition, evaluation/modification by a health care provider is not essential. It is also possible to make a system that does not require manual correction by accumulation of data.

Figure 12:
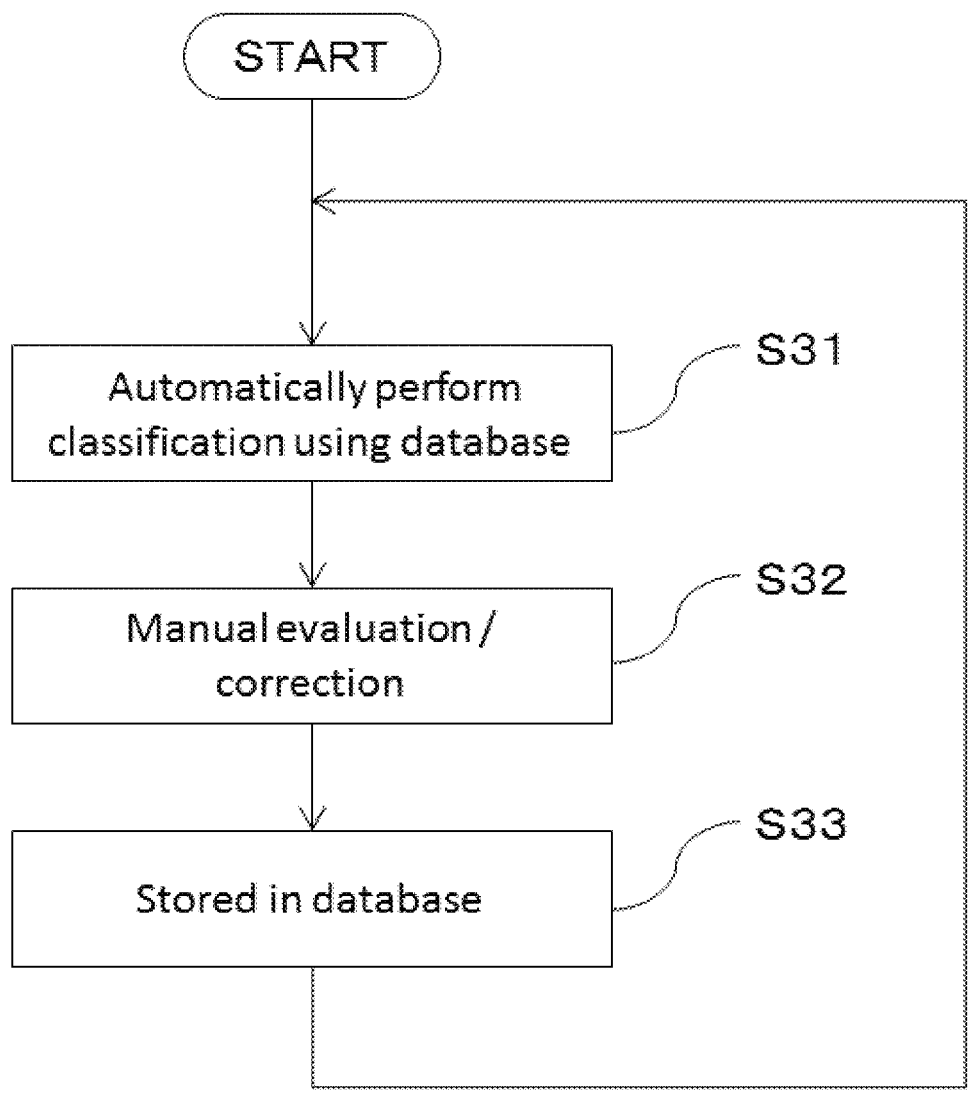
FIG. 12 shows a flow diagram of the use and accumulation of medical image data.

FIG. 12 shows a flow diagram of the use and accumulation of medical image data. As shown in FIG. 12, in the medical information virtual reality system of the present embodiment, classification is automatically performed using a database (S31). Next, evaluation and correction are performed by the health care provider (S32). The result of the classification is stored in the database (S33). The steps mentioned above are repeatedly performed.

Here, the results of classification to be stored include not only the final result that has been evaluated and corrected by the health care provider but also the difference between the results of automatic classification and the results of manual classification, etc., and the accumulation of such data enables automatic segmentation with higher accuracy.

By performing the segmentation as described above, tagging becomes easy. As a method of tagging, it can be performed for the whole living body from which data is to be acquired, or for each segment such as an organ or a blood vessel. For example, when tagging is performed by age, tagging is performed for the whole living body. In addition, in the case of tagging a site with a tumor, tagging is performed with respect to an organ having a tumor or a tumor site segmented into an organ having a tumor.

In addition, it is possible to tag specific 3-dimensional coordinates regardless of each segment, or to tag by setting a spatial range.

As types of tagging, marking, numerical input, comments in text, etc. are possible. For example, although the age of the living body and so on is numerically input, when a qualitative comment is recorded, a comment can be made by text. In addition, markers can be used to mark the 3-dimensional space.

Embodiment 4

Figure 9:
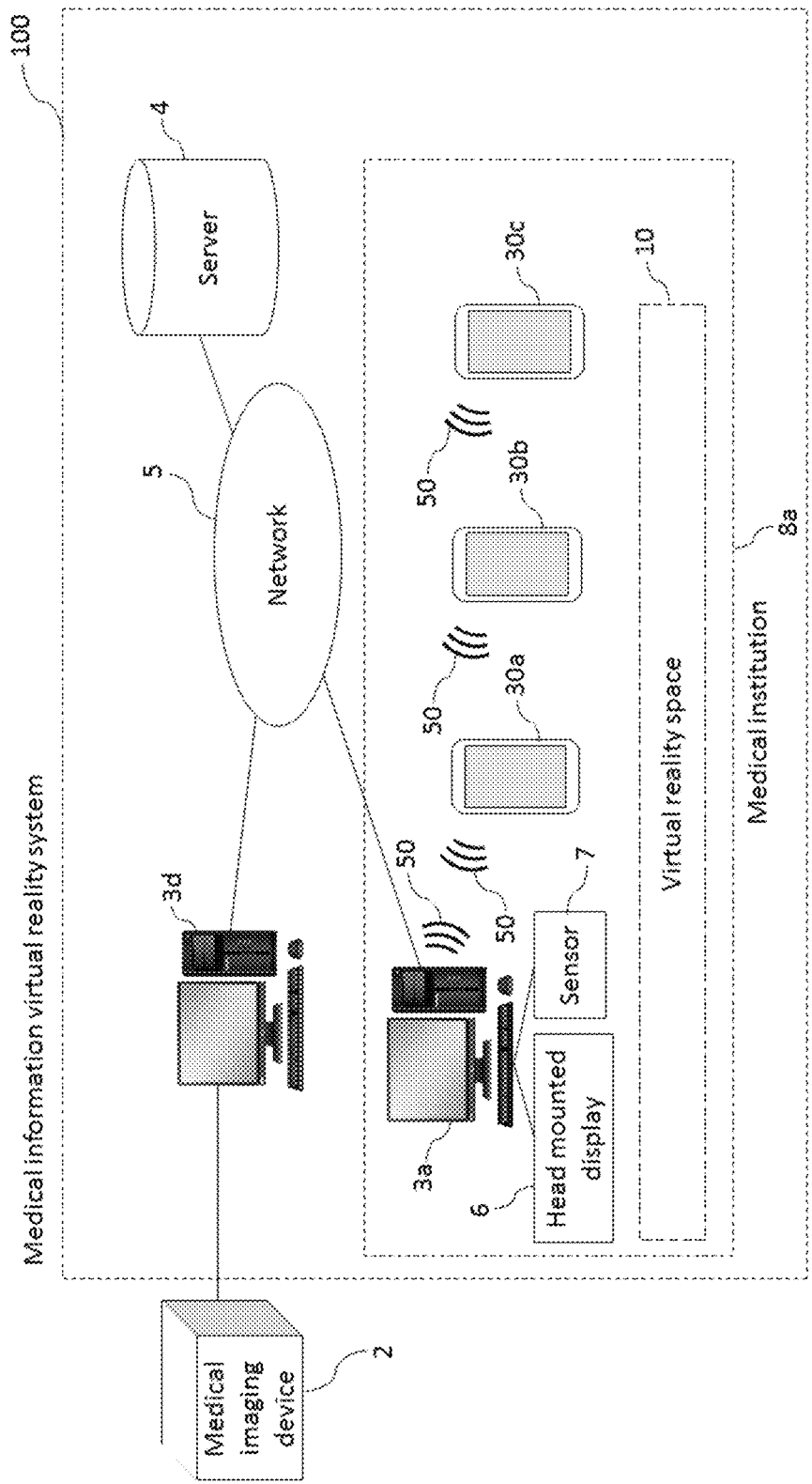
FIG. 9 shows a system configuration diagram of a medical information virtual reality system of Embodiment 4.

FIG. 9 shows a system configuration diagram of a medical information virtual reality system of Embodiment 4.

As shown in FIG. 9, the medical information virtual reality system 100 includes PCs (3a, 3d), smart phones (30a to 30c), a server 4, a network 5, a head mounted display 6, and a sensor 7.

The medical institution 8a is furnished with a PC 3a, smart phones (30a to 30c), a head mounted display 6, and a sensor 7. The smartphones (30a to 30c) are connected to the PC 3a via the network 50. The PC 3a is connected to the head mounted display 6 and the sensor 7 via a wire or wirelessly. Although the head mounted display 6 and the sensor 7 are not connected to the smartphones (30a to 30c), a smartphone VR application (not shown) for using the medical information virtual reality system 100 is installed, realizing a structure that allows simultaneous viewing of the virtual reality space 10 expressed by using PC 3a, the head mounted display 6 and a sensor 7.

As a specific structure, a virtual reality application (not shown) installed on PC 3a and a virtual reality application (not shown) installed on smartphones (30a to 30c) are connected by a network 50. In the present embodiment, the network 50 is shown to be communicating wirelessly, but this may be a wired communication. The position information of the head mounted display 6 acquired using the sensor 7 in the virtual reality application of the PC 3a and the information of the controller (not shown) are transmitted to the smartphones (30a to 30c), and in the smartphones (30a to 30c), the virtual reality space 10 can be viewed at the same position in the virtual reality space as the position wherein user views the virtual reality space 10 in the head mounted display 6. Also, the virtual reality space 10 can be viewed by changing the angle based on the operation of the screen of the smartphones (30a to 30c). The position information of the controller is sensed not only by the position of the controller but also by the orientation of the controller by the sensor 7, and accordingly, the motion of the hand of the user using the virtual reality application in the PC 3a can be viewed on the virtual reality space which a smartphone (30a to 30c) displays. Namely, the user using the head mounted display 6 or the controller and the users using the smartphones (30a to 30c) can recognize the virtual reality space that matches the respective position information upon sharing the same virtual reality space.

As described here, by using the smartphone, the virtual reality system can be used easily and inexpensively, even when there are many participants.

Figure 10:
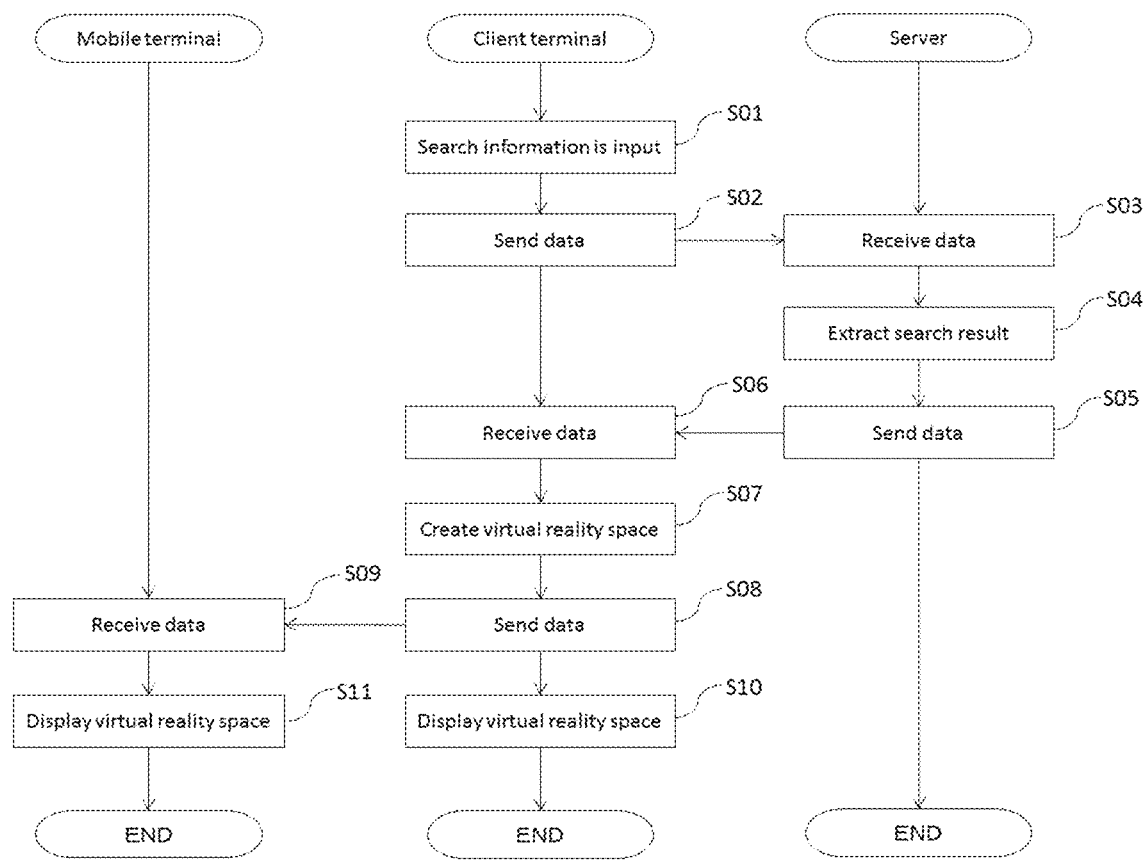
FIG. 10 shows a data flow diagram of the medical information virtual reality system of Embodiment 4.

FIG. 10 shows a data flow diagram of the medical information virtual reality system of Embodiment 4. As shown in FIG. 10, first, search information is input in the client terminal (S01). Data on search information is transmitted to the server (S02). The server receives the data (S03). The server performs a search and extracts a search result (S04). The search result is transmitted from the server to the client terminal (S05). The client terminal receives the search result (S06). The client terminal creates a virtual reality space based on the search result (S07). Data constituting the created virtual reality space is transmitted from the client terminal to the mobile terminal (S08). The mobile terminal receives the data constituting the virtual reality space (S09). The virtual reality space is displayed on the client terminal (S10). In the mobile terminal, a virtual reality space is displayed (S11).

Embodiment 5

Figure 13:
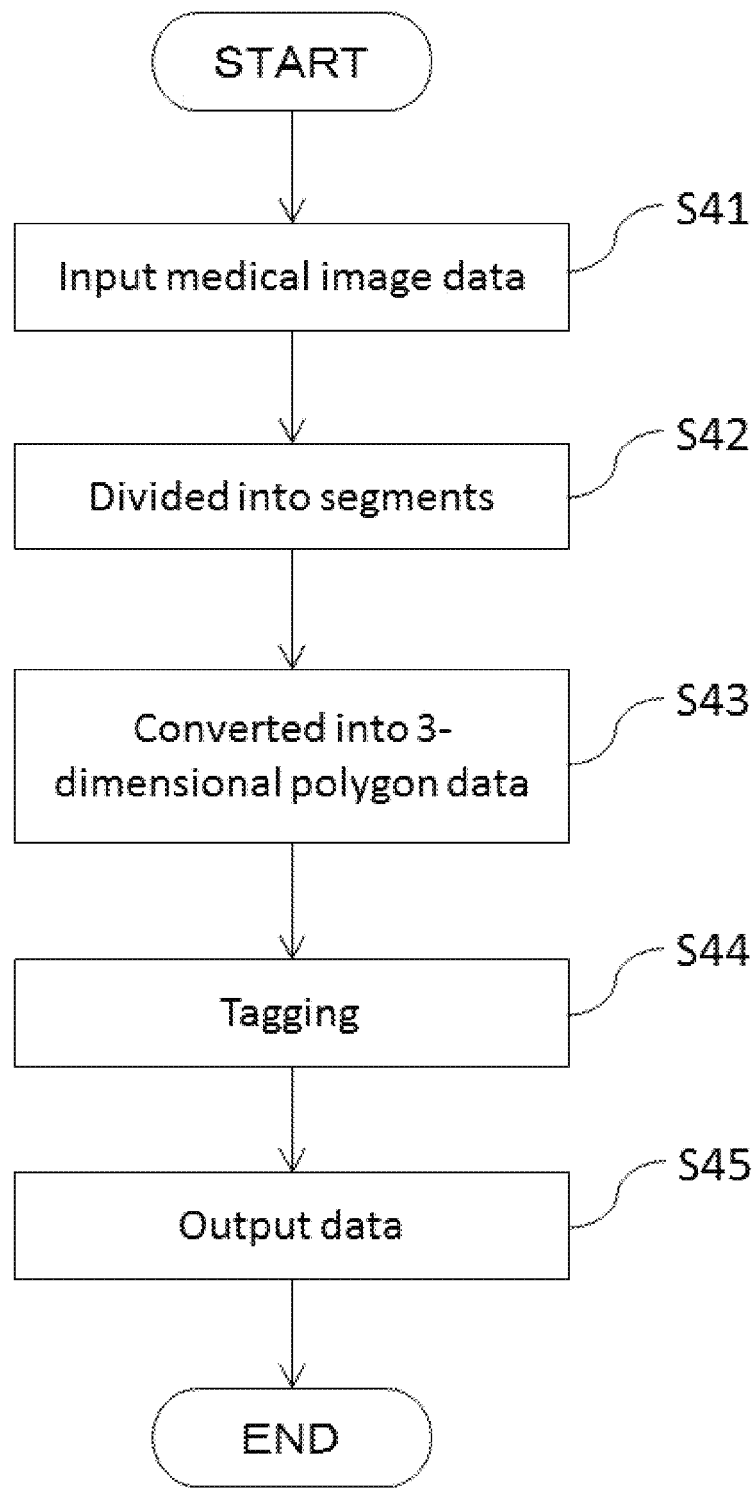
FIG. 13 shows a production flow diagram 1 of medical information virtual reality data of Embodiment 5.
Figure 14:
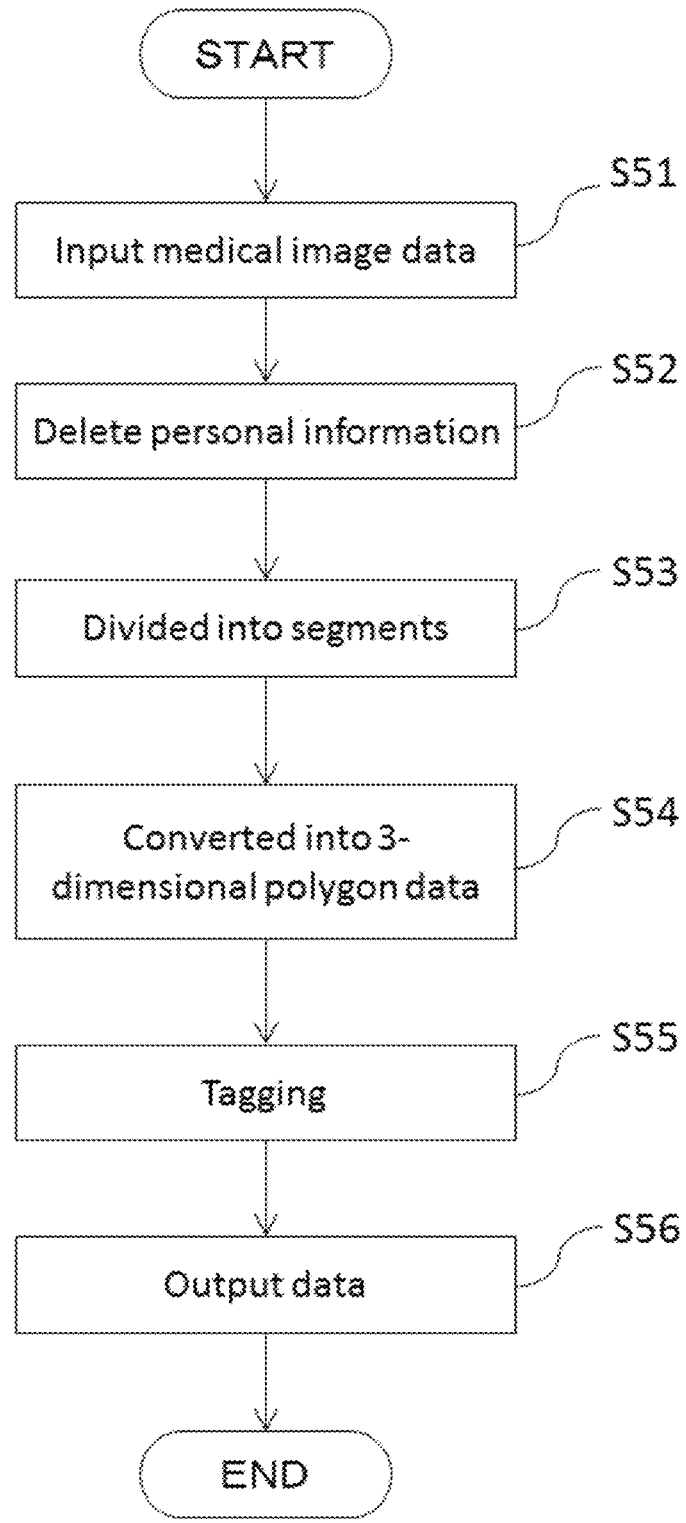
FIG. 14 shows a production flow diagram 2 of medical information virtual reality data of Embodiment 5.
Figure 15:
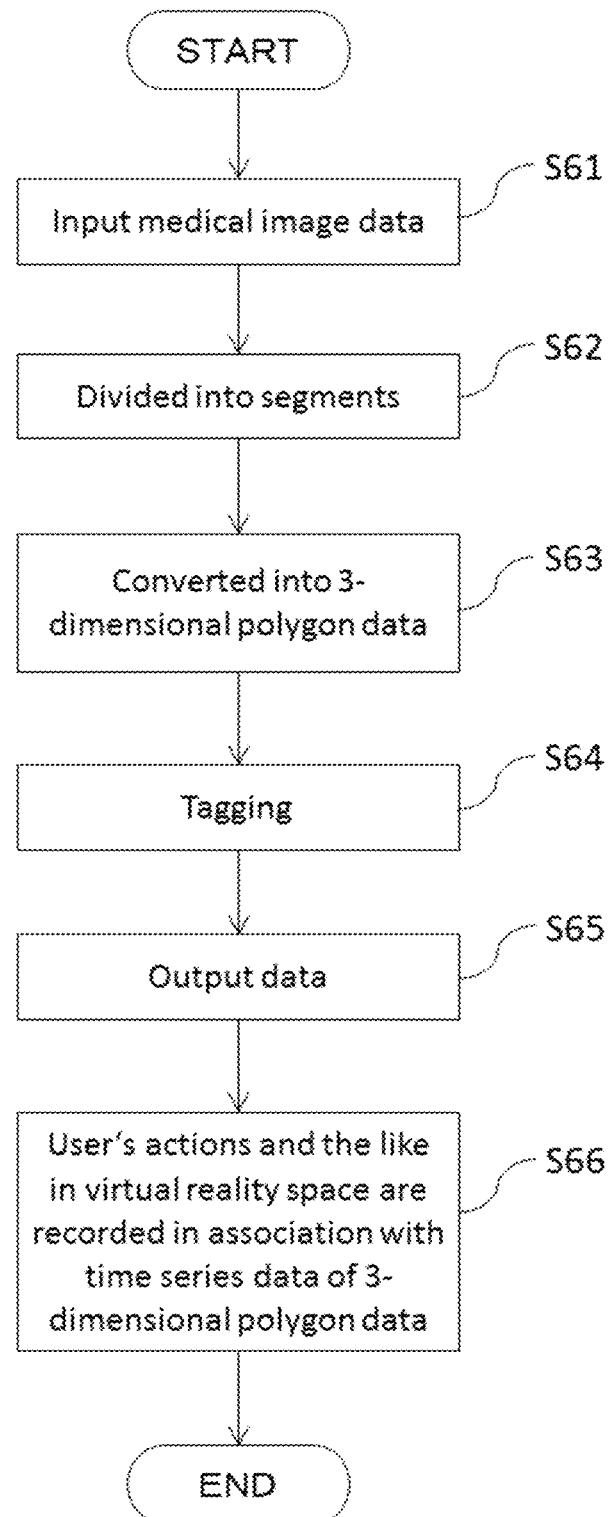
FIG. 15 shows a production flow diagram 3 of medical information virtual reality data of Embodiment 5.

FIG. 13 to FIG. 15 show a production flow diagram of medical information virtual reality data of Embodiment 5. First, as shown in FIG. 13, when producing medical information virtual reality data, medical image data is input to the medical information virtual reality server system 1 (S41). Next, each feature site is classified and divided into segments by using at least any one of 2-dimensional medical image data of CT image data, MRI image data or ultrasonic image data or 3-dimensional position measurement data of a living body part, implant, medical device, index marker or a feature part of an insertion object (S42). Medical image data is converted into 3-dimensional polygon data having segments (S43). And the image data is tagged to the 3-dimensional polygon data or segment (S44). The 3-dimensional polygon data is stored in the database and output based on the attached tag (S45).

As a configuration different from the above, a configuration may be considered in which personal information present in medical image data is deleted. For example, as shown in FIG. 14, after medical image data has been input (S51), personal information is deleted (S52), and then divided into segments for each characteristic portion using any of the medical image data described above (S53). Here, deletion of personal information does not have to be after input of medical image data, and a method of inputting medical image data wherefrom personal information has already been deleted may be employed.

Note that the flow after division into segments (S53) is the same as that in FIG. 13.

Furthermore, as a configuration different from the above, a procedure is considered, wherein the data when the user experiences virtual reality space is recorded and transmitted to the medical information virtual reality server system 1 by utilizing the 3-dimensional polygon data output from the medical information virtual reality server system 1, which is made to be a database of higher usability. For example, as shown in FIG. 15, after the data is output from the medical information virtual reality server system 1 (S65), it is possible to create medical information virtual reality data having higher usability by storing data in which the user's actions and the like in the virtual reality space are recorded in association with time series data of 3-dimensional polygon data (S66).

Note that the flow before data output (S65) from the medical information virtual reality server system 1 is the same as that in FIG. 13.

INDUSTRIAL APPLICABILITY

The present invention is useful as a system for health care providers to improve communication within a team in diagnosis, learning, training, research, and treatment, and further as a system for conducting explanation to patients.

DESCRIPTION OF SYMBOLS

1 Medical information virtual reality server system
1*a*, 1*b*, 100 Medical information virtual reality system
2 Medical imaging device
3, 3*a*, 3*b* PC
4 Server
5, 50 Network
6 Head mounted display
7 Sensor
8*a* Medical institution
8*b* Educational institution
8*c* Health institution
10 Virtual reality space
11 Medical image data acquisition means
12 Personal information deletion means
13 Dividing means
14 Medical image data conversion means
15 Tagging means
16 3-dimensional polygon data management means
17 Input means
18 Output means
20 Liver
21 Portal vein
22 Pancreas
23 Kidney
24 Aorta
25 Heart
26 Ribs
27 Spleen
28 Spine
29 Pelvis
30 Gallbladder

What is claimed is:

1. A method of creating medical information virtual reality data suitable for displaying a virtual reality space interactively to a user, the method comprising:
    sectioning medical image data into segments for respective feature parts by computer execution of a medical information virtual reality program, the medical image data including at least one of the following: two-dimensional medical image data, computed tomography image data, magnetic resonance imaging data, ultrasonic image data, three-dimensional position measurement data of a biological part, three-dimensional position measurement data of an implant, three-dimensional position measurement data of a medical device, an index marker of a feature part of a furnished object, or three-dimensional position measurement data of a feature part of a furnished object;
    converting medical image data into three-dimensional polygon data having segments by computer execution of the medical information virtual reality program;
    tagging three-dimensional polygon data or segments thereof by computer execution of the medical information virtual reality program;
    associating three-dimensional polygon data with an arbitrary world coordinate position by computer execution of the medical information virtual reality program; and
    associating time-series data recorded with a user's motion in a virtual reality space by computer execution of the medical information virtual reality program, based on the three-dimensional polygon data and changes of the virtual reality space based on the motion, with time-series data of three-dimensional polygon data.

2. The method of claim 1, further comprising deleting personal information that is linked to at least part of the medical image data.

3. A medical information virtual reality server, said server connectable to a client via a network for transmitting and receiving data to interactively display a virtual reality space to a user, said server comprising a computer configured by a program to perform at least the following:
    input medical image data;
    segment medical image data into segments for respective characteristic sites, the characteristic sites including at least one of the following: a living body site, an implant, a medical device, an index marker, or a mounting object;
    convert medical image data into three-dimensional polygon data having segments;
    tag three-dimensional polygon data or segments thereof;

associate three-dimensional polygon data with an arbitrary world coordinate position;
store three-dimensional polygon data in a database;
receive tag information from the client;
extract three-dimensional polygon data thereof based on the received tag information and send it to the client; and
receive from the client a user's motion in a virtual reality space based on the three-dimensional polygon data and on changes in the virtual reality space based on the motion.

4. The server of claim 3, wherein the program is further configured to delete personal information that is linked to at least part of the medical image data.

5. The server of claim 3, wherein the program is configured to segment medical image data into segments based at least in part on differences in image density or on three-dimensional position coordinate information when the medical image data includes two-dimensional medical image data.

6. The server of claim 3, wherein the medical image data includes at least one of the following: two-dimensional computed tomography image data, two-dimensional magnetic resonance imaging data, two-dimensional ultrasonic image data, three-dimensional position measurement data of an implant, or three-dimensional position measurement data of a characteristic site.

7. The server of claim 3, wherein the program is further configured to correct segments of three-dimensional polygon data and section data into corrected segments.

8. The server of claim 3, wherein the program is further configured to correct segments based on medical image data and divide segments into corrected segments.

9. The server of claim 3, wherein the program is further configured to store in the database a time series obtained at least in part by transforming past medical image data.

10. The server of claim 3, wherein the program is further configured to store in the database as a time series, shape changes in three-dimensional polygon data.

11. The server of claim 3, wherein the program is further configured to store in the database a visual field and an action of the user in the virtual reality space, with time series data of three-dimensional polygon data.

12. The server of claim 3, wherein the program is further configured to store in the database a change of a three-dimensional shape of a feature part accompanying a user's flexural deformation in a virtual reality space, using three-dimensional polygon data as time series data.

13. The server of claim 3, wherein the program is further configured to add or superimpose three-dimensional polygon data generated from data other than the medical image data, and to set an origin of the resulting converged three-dimensional polygon data.

14. The server of claim 3, wherein the living body site includes a biological part to be divided into segments, and the biological part includes at least one of the following: an organ, a blood vessel, a lesion, a nerve, a membrane, a body liquid, or blood.

15. A medical information virtual reality system comprising:
a client including a computer configured by a client program to interactively display a virtual reality space to a user;
a medical information virtual reality server connected to the client via a network for transmitting and receiving data;
the client computer configured to transmit, to the medical information virtual reality server, tag information input to the client by the user;
the server including a computer configured by a server program to extract three-dimensional polygon data having tag information and segments for respective feature parts of medical image data and being based on the received tag information, and to transmit extracted three-dimensional polygon data to the client;
the client computer configured to display the virtual reality space based on the received three-dimensional polygon data, the client computer also configured to record the user's motion in the virtual reality space and to and transmit said motion to the server and to change the virtual reality space based on said motion.

16. The system of claim 15, wherein the client is connected to at least one mobile terminal via a wire or wirelessly, and transmits data of the virtual reality space created in the client to the mobile terminal, and on the mobile terminal a virtual reality space based on the received data is displayed.

* * * * *